United States Patent [19]

Miller et al.

[11] Patent Number: 5,763,452
[45] Date of Patent: Jun. 9, 1998

[54] PHARMACEUTICAL COMPOSITIONS AND USAGES

[75] Inventors: Ronald Brown Miller, Basel, Switzerland; Allan John Miller, Surrey; Stephen Gordon Douglas, Shropshire, both of England

[73] Assignee: Euro-Celtique, S.A., Luxembourg, Luxembourg

[21] Appl. No.: 584,658

[22] Filed: Jan. 11, 1996

Related U.S. Application Data

[63] Continuation of Ser. No. 310,640, Sep. 22, 1994, abandoned.

[30] Foreign Application Priority Data

Sep. 22, 1993 [GB] United Kingdom ............... 9319568

[51] Int. Cl.⁶ ........................... A61K 31/41; A61K 31/40
[52] U.S. Cl. ........................................ 514/282; 514/420
[58] Field of Search ........................... 514/420, 282

[56] References Cited

U.S. PATENT DOCUMENTS 4,571,400  2/1986  Arnold .................................. 514/282

FOREIGN PATENT DOCUMENTS

0535841A1  9/1992  European Pat. Off. ..... A61K 31/485

OTHER PUBLICATIONS

N. Bhu, et al. "Efficacy and safety of an ibuprofen and dextropropoxyphene combination (Ibudex) in medical practice", The British Journal of Clinical Practice, Nov. 1986, vol. 40, No. 11, (pp. 482–485).

*Primary Examiner*—Theodore J. Criares
*Attorney, Agent, or Firm*—Steinberg, Raskin & Davidson, P.C.

[57] ABSTRACT

The invention relates to the use of a non-steroidal anti-inflammatory drug together with an opioid analgesic in the manufacture of a medicament for the treatment of arthritis.

13 Claims, 9 Drawing Sheets

FIG 4. Mean Clinical Score with Low Dose Treatment.
p < 0.01 vs indomethacin group.

FIG 6. Mean radiological score with low dose treatment.

FIG. 7B  Clinical Score and Footpad Diameter in Adjuvant Arthritis

FIG. 8B Radiological and Histological Scores in Adjuvant Arthritis

FIG. 9B Inhibition of Plasma Extravasation in Day 5 mBSA Arthritis

PHARMACEUTICAL COMPOSITIONS AND USAGES

This is a continuation of application Ser. No. 08/310,640, filed Sep. 22, 1994, now abandoned, which is incorporated by reference herein in its entirety.

BACKGROUND OF THE INVENTION

This invention relates to the treatment of arthritis and to pharmaceutical compositions and usages therefor.

In general, the treatment of arthritic conditions has been limited to symptomatic treatment, for example to relieve symptoms such as inflammation and pain. Thus, for example, it has been proposed to use so-called non-steroidal anti-inflammatory drug (NSAID's) in the treatment of arthritic conditions. It has also been proposed to use a variety of analgesics, including opioid analgesics, in the relief of pain in arthritic conditions.

It has now been found, in accordance with the present invention, that the treatment of arthritic conditions with both (i) an NSAID, and (ii) an opioid analgesic can serve to treat the arthritic condition itself, that is to inhibit the arthritic process.

Accordingly, one embodiment of the present invention provides the use of an NSAID together with an opioid analgesic in the manufacture of a medicament for the treatment of arthritis (both osteoarthritis and rheumatoid arthritis). The invention also provides a method for the treatment of arthritis by the administration to a patient of an NSAID together with an opioid analgesic. The invention further provides certain pharmaceutical compositions containing an NSAID and an opioid analgesic.

BRIEF DESCRIPTION OF THE DRAWINGS

The following drawings are illustrative of embodiments of the invention and are not meant to limit the scope of the invention as encompassed by the claims.

DETAILED DESCRIPTION

The inhibition of the disease process may be manifested, e.g., by a reduction in the mean radiological score of a patient who has undergone or who is undergoing treatment in accordance with the invention. Other parameters which could be indicative of an inhibition of the arthritic disease process by treatment in accordance with this invention are joint diameter, plasma extravasation and histology.

Example of NSAID's which may be used in accordance with the present invention include, but are not limited to, diclofenac, flurbiprofen, ibuprofen, indomethacin, ketoprofen and naproxen or pharmaceutically acceptable salts thereof. Examples of opioid analgesics which may be used in accordance with the invention include, but are not limited to, morphine, hydromorphone, codeine dextropropoxyphene, oxycodone, hydrocodone, and dihydrocodeine, and their pharmaceutically acceptable salts. Examples of particular NSAID/opioid analgesic combinations which may be mentioned include indomethacin/morphine, ibuprofen/codeine and diclofenac/codeine.

The daily dosage rates of opioid and analgesic and NSAID will depend upon the nature of the particular active ingredients used. By way of example, for a combination of morphine sulphate and indomethacin, the morphine sulphate dosage is suitably 5–300 mg, preferably 5–200 mg, more preferably 5–60 mg (e.g. 10–60 mg or 10–40 mg) and the indomethacin dosage is suitably 5–300 mg (eg. 40–200 mg), preferably 10–200 mg, more preferably 20–80 mg; for a diclofenac/codeine phosphate combination, the diclofenac dosage is suitably 10–200 mg (eg. 25–200 mg), preferably 10–150 mg (eg. 75–100 mg), and more preferably 20–80 mg, and the codeine phosphate dosage is suitably 12.5–310 mg, preferably 20–200 mg, more preferably 40–120 mg (eg. 37.5–150 mg); and for an ibuprofen/codeine combination, the ibuprofen dosage is suitably 300–2400 mg, preferably 400–2400 mg, more preferably 400–1200 mg (e.g. 480–1200 mg), and the codeine dosage is suitably as mentioned above.

In the case of combinations utilizing dextropropoxyphene as the opioid the total daily dosage of dextropropoxyphene may be 32.5–260 mg, preferably 65–130 mg; in the case of dihydrocodeine (DHC) being the opioid of a combination for use in accordance with the invention the total daily dosage of DHC may be 20–180 mg, preferably 30–90 mg.

The foregoing dosages may represent total daily dosages for a patient undergoing treatment to inhibit the arthritic disease process. When the dosage is provided in a delayed or sustained release form, the total dosage or appropriate sub-division of the total dosage of each active ingredient will be provided in the unit dosage form. For instance, a unit dosage form for the combination of indomethacin and morphine sulphate suitable for twice daily dosing may contain, eg., 2.5–150 mg, preferably 2.5–30 mg or 5–20 mg morphine sulphate and 2.5–150 mg, preferably 5–100 mg or 10–40 mg indomethacin. In the case of the combination of ibuprofen and codeine, for example, a unit dosage form for twice daily dosing may contain 150–1,200 mg, preferably 200–1,200 mg or 200–600 mg ibuprofen and 5–150 mg, preferably 10–100 mg or 20–60 mg codeine; while for the combination of diclofenac and codeine a unit dosage form for twice daily dosing may contain 5–100 mg, preferably 5–75 mg or 10–40 mg diclofenac and the above mentioned dosage of codeine. Unit dosages for twice daily dosing with combinations containing dextropropoxyphene may contain 16.25–130 mg, preferably 32.5–65 mg and those containing DHC may contain 10–90 mg, preferably 15–45 mg of DHC. Different combinations may incorporate the amounts of active ingredients given above.

Unit dosage forms containing those active ingredients which are intended for either once a day dosing or more frequent dosing than twice a day may contain appropriately greater or lesser amounts of the active ingredients.

Other particularly suitable combinations may be dihydrocodeine and ibuprofen; dihydrocodeine and diclofenac; dextropropoxyphene and ibuprofen and dextropropoxyphene and diclofenac, at the above mentioned suitable dosages.

It is generally desirable that the NSAID dosage be kept relatively low since prolonged administration of NSAID's at high dosages can, in itself, lead to bone or cartilage destruction.

Medicaments produced using the NSAID and opioid analgesic (simply, hereinafter, medicaments of the invention) may take a wide variety of forms but are preferably suitable for oral administration and, in this case, are especially preferred to be in unit dosage form although bulk forms such as syrups, suspensions or linctuses may also be employed. Where the medicament is in unit dosage form it may, for example, be in the form of a tablet or filled capsule (filled with a liquid fill or a particulate or solid fill). The unit dosage form may be formulated to give immediate release of the active ingredients upon administration or may be adapted to give delayed or sustained release or, in indeed, a combination of both immediate and delayed or sustained release.

Suitable materials for inclusion in a controlled release matrix include, for example (a) Hydrophilic or hydrophobic polymers, such as gums, cellulose esters, cellulose ethers, protein derived materials, nylon acrylic resins, polylactic acid, polyvinylchloride, starches, polyvinylpyrrolidones, and cellulose acetate phthalate. Of these polymers, cellulose ethers especially substituted cellulose ethers such as alkylcelluloses (such as ethylcellulose), $C_1$–$C_6$ hydroxyalkylcelluloses (such as hydroxypropylcellulose and especially hydroxyethyl cellulose) and acrylic resins (for example methacrylates such as methacrylic acid copolymers) are preferred. The controlled release matrix may conveniently contain between 1% and 80% (by weight) of the hydrophilic or hydrophobic polymer.

(b) Digestible, long chain ($C_8$–$C_{50}$, especially $C_8$–$C_{40}$), substituted or unsubstituted hydrocarbons, such as fatty acids, hydrogenated vegetable oils such as Cutina (Trade Mark), fatty alcohols (such as lauryl, myristyl, stearyl, cetyl or preferably cetostearyl alcohol), glyceryl esters of fatty acids for example glyceryl monostearate mineral oils and waxes (such as beeswax, glycowax, castor wax or carnauba wax). Hydrocarbons having a melting point of between 25° C. and 90° C. are preferred. Of these long chain hydrocarbon materials, fatty (aliphatic) alcohols are preferred. The matrix may contain up to 60% (by weight) of at least one digestible, long chain hydrocarbon.

(c) Polyalkylene glycols. The matrix may contain up to 60% (by weight) of at least one polyalkylene glycol.

A suitable matrix comprises one or more cellulose ethers or acrylic resins, one or more $C_{12}$–$C_{36}$, preferably $C_{14}$–$C_{22}$, aliphatic alcohols and/or one or more hydrogenated vegetable oils.

A particularly suitable matrix comprises one or more alkylcelluloses, one or more $C_{12}$–$C_{36}$, (preferably $C_{14}$–$C_{22}$) aliphatic alcohols and optionally one or more polyalkylene glycols.

Preferably the matrix contains between 0.5% and 60%, especially between 1% and 50% (by weight) of the cellulose ether.

The acrylic resin is preferably a methacrylate such as methacrylic acid copolymer USNF Type A (Eudragit L, Trade Mark), Type B (Eudragit S, Trade Mark), Type C (Eudragit L 100-55, Trade Mark), Eudragit NE 30D, Eudragit E, Edüragit RL and Eudragit RS. Preferably the matrix contains between 0.5% and 60% by weight, particularly between 1% and 50% by weight of the acrylic resin.

In the absence of polyalkylene glycol, the matrix preferably contains between 1% and 40%, especially between 2% and 36% (by weight) of the aliphatic alcohol. When polyalkylene glycol is present in the oral dosage form, then the combined weight of the aliphatic alcohol and the polyalkylene glycol preferably constitutes between 2% and 40%, especially between 2 and 36% (by weight) of the matrix.

The polyalkylene glycol may be, for example, polypropylene glycol or, which is preferred, polyethylene glycol. The number average molecular weight of the at least one polyalkylene glycol is preferably between 200 and 15000 especially between 400 and 12000.

The medicament-containing controlled release matrix can readily be prepared by dispersing the active ingredient in the controlled release system using conventional pharmaceutical techniques such as wet granulation, dry blending, dry granulation or coprecipitation.

Sustained release formulation may also be produced by spheronizing the active ingredient(s) with a spheronizing agent such as microcrystalline cellulose. Further, the active ingredients my be melt pelletized in conjunction with a hydrophobic fusible carrier, for example hydrogenated castor oil, hydrogenated vegetable oil, beeswax or carnauba wax. If desired, a dissolution release control agent may be employed together with the fusible carriers and examples of such include water-soluble organic materials such as polyalkylene glycols or powdered solids such as dicalcium phosphate.

The content of NSAID and opioid analgesic in any particular dosage form will depend upon a number of variables including the number of doses intended to be administered per day and the intended daily dosage.

The effectiveness of an NSAID/opioid analgesic combination hag been evidenced by animal tests.

Polyarthritis was induced in 14 groups of rats (n=6 per group) via an injection of adjuvant material into the base of the tail. Two naive groups were used as controls (n=6 per group). Each group received a different regimen of treatment, i.e., indomethacin, morphine or combination (i.e. morphine+indomethacin) in either high or low doses, from day 0 or when a clinical sign of adjuvant disease first became apparent. The arthritic control group received no treatment over the course of the experiment. Daily during the experiment, footpad diameters and clinical scores were measured. On day 21 the rats were sacrificed and their hindlimbs radiographed.

DETAILED DESCRIPTION OF PREFERRED EMBODIMENTS

EXAMPLE 1

Male Wistar rats weighing 200–300 g, were kept in groups of 6, in cages maintained at a temperature of 20° C. with 12 hours light, cleaned weekly and fed lab chow and water ad libitum.

Acute polyarthritis was induced by a single intradermal injection of 0.1 mull of 10 mg/mull suspension of adjuvant (heat killed mycobacterium tuberculosis in sterile paraffin oil), into the base of the tail. Naive animals were used as controls.

The exclusion criteria for the study were lethargy, poor fur condition, nasal discharge and diarrhea.

Chronic administration of the two experimental drugs, morphine and indomethacin, was performed by daily dosing.

(1) Morphine in 0.1% sodium metabisulphate (Martindale Pharmaceuticals), was diluted to 5 ml/ml and 0.5 mg/ml in 0.9% sterile saline. The morphine was administered as a bolus by intraperitoneal injection.

(2) Indomethacin (Sigma), 2.5 mg/ml and 0.5 mg/ml solutions were prepared in 2% sodium bicarbonate. The pH was then adjusted to 7. The indomethacin was administered as a bolus orally.

The rats were divided into the following experimental groups:

A—HIGH DOSE GROUPS

Group 1 Morphine 5 mg/kg/day given from the onset of clinically apparent disease.

Group 2 Indomethacin 2.5 mg/kg/day given from the onset of clinically apparent disease.

Group 3 Morphine 5 mg/kg/day and indomethacin 2.5 mg/kg/day given from the onset of clinically apparent disease.

Group 4 Arthritic control group.

Group 5 Naive control group.

B—LOW DOSE GROUPS

Group 6 Morphine 0.5 mg/kg/day given from the day onset of clinically apparent disease.

Group 7 Indomethacin 0.5 mg/kg/day given from the onset of clinically apparent disease.

Group 8 Morphine 0.5 mg/kg/day and indomethacin 0.5 mg/kg/day given from onset of clinically apparent disease.

Group 9 Arthritic control group.

Group 10 Naive control group.

DISEASE ASSESSMENT

The rats were examined daily, over the 21 day period for the following parameters:

(a) CLINICAL SCORE

The rats were clinically scored, as described below.

Clinical score 0=No inflammation.

Clinical score of 1=Slight redness and swelling of the foot.

Clinical score of 2=Foot swelling such that tendons were no longer visible.

Clinical score of 3=Gross inflammation and deformity of the ankle joint.

(b) HINDLIMB FOOTPAD DIAMETER

The footpad diameter of both hindlimbs were measured using vernier callipers at a designated level/point on the rats hindlimb (in millimeters).

(c) RADIOLOGICAL ASSESSMENT

Using a faxitron machine, hind limbs were exposed to the x-ray source for 25 minutes (5×5 minute exposures) at 40 KVP. X-ray films were developed, fixed and then placed in slides for view on an overhead projector for assessment.

Each radiograph of the rat hindfoot, was evaluated blindly for the presence and severity of the following parameters.

(1) Bone mineralization

Grade 0=Normal.

Grade 1=Mild juxtaarticular osteoporosis only.

Grade 4=Severe osteoporosis with pathologic fractures.

(2) Erosions

Grade 0=None.

Grade 1=Small bony irregularities at corners of articular surfaces.

Grade 4=Complete destruction of articular surfaces.

(3) Periostitis

Grade 0=None.

Grade 1=Thin delicate layer of subperiosteal new bone involving the distal tibia or plantar surface of the tarsus.

Grade 4=severe irregular bony proliferation cloaking the entire ankle region.

(4) Cartilage space

Grade 0=Normal.

Grade 1=Slight joint space narrowing.

Grade 4=Bony ankylosis and destruction of cartilage.

(5) Soft tissue swelling

Grade 0=Normal.

Grade 1=Slight particular soft tissue swelling.

Each radiograph was scored blindly of the presence and severity of the five parameters shown above.

A grade of 0 to 4 (with 0 equalling normal and 4 equalling severe changes as stipulated above) was assigned for each of the above five possible findings. A total score of the sum of each individual grade for any given rat was then obtained. Thus the maximum total score any rat could receive was 20.

The results obtained are shown graphically in FIGS. 1–6 of the accompanying drawings.

EXAMPLE 2

A further adjuvant arthritis study was carried out using a protocol similar to that of Experimental 1 (see also "Models for Arthritis, the search for anti-arthritic drugs" Chapter 1, Billingham M.E.T., 1990 pages 1–47, Pergammon Press). The effects of morphine and indomethacin given alone or in combination on clinical score and joint diameter; and radiological and histological scores were assessed. The results of this study are shown in FIGS. 7 and 8.

Figure 1:
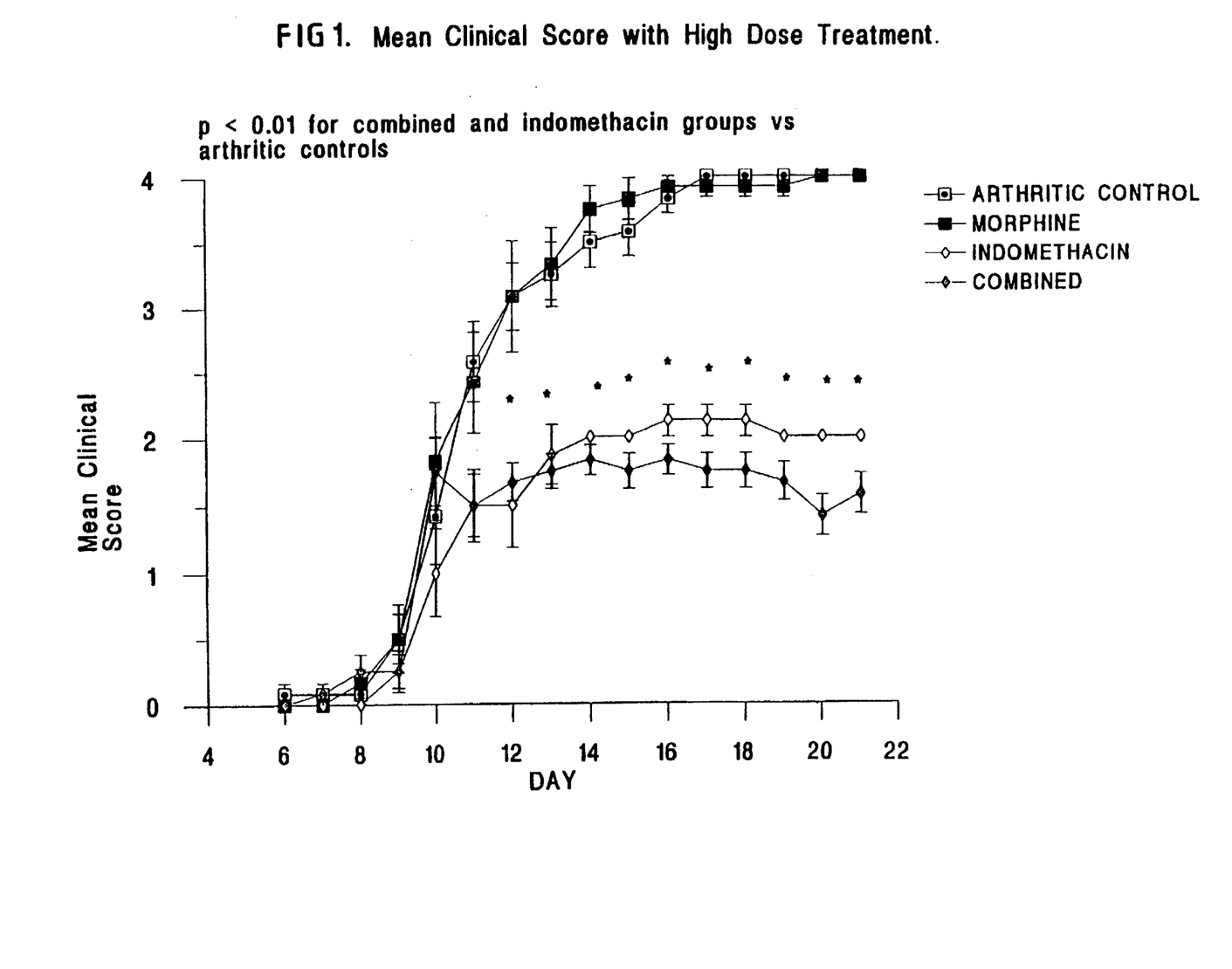
FIG. 1 is a graphical representation of the mean clinical score per day achieved with high dose treatment of arthritic rats using morphine, indomethacin and a combination of morphine and indomethacin versus a control.
Figure 2:
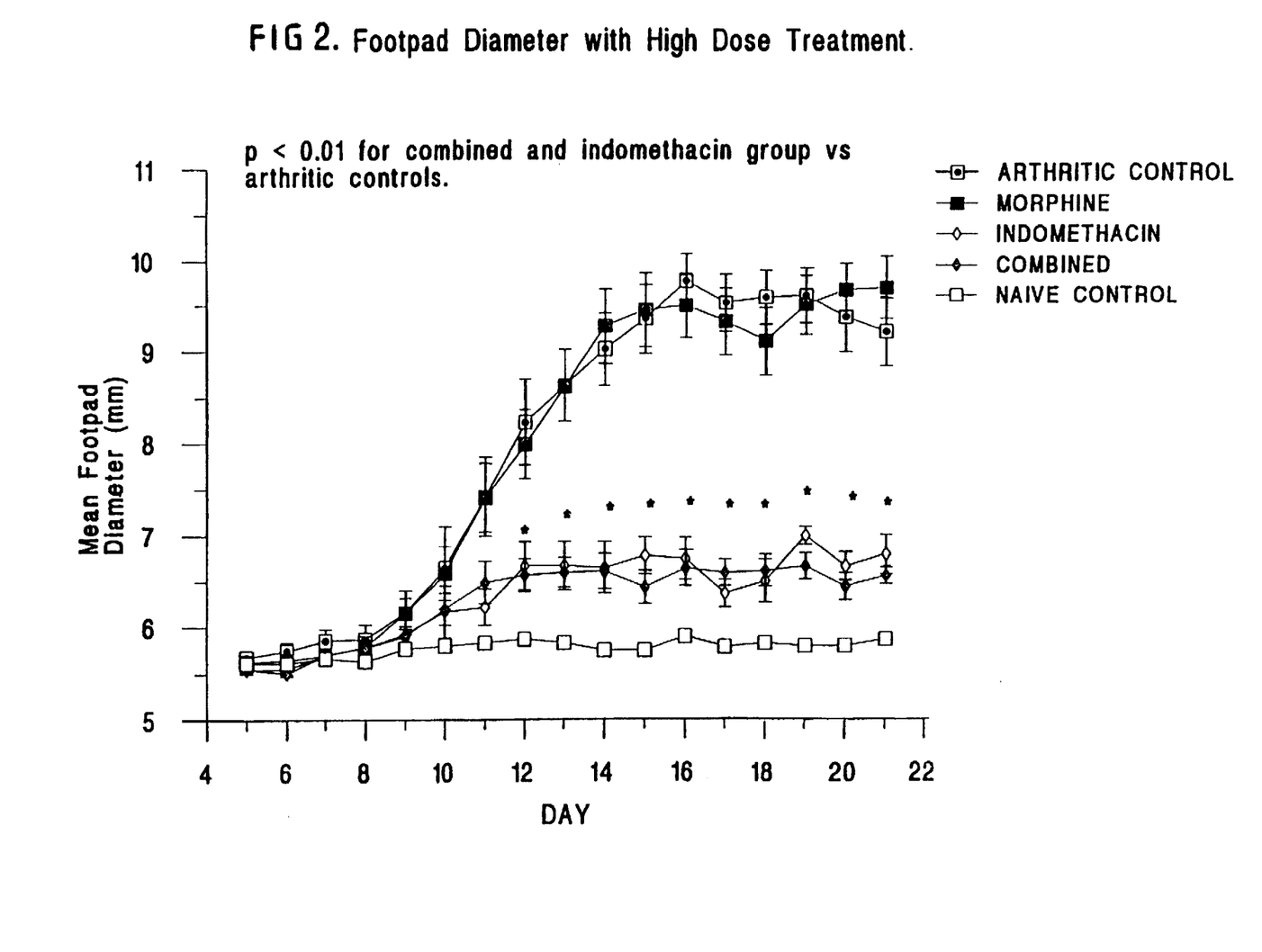
FIG. 2 is a graphical representation of the mean foot pad diameter per day achieved during high dose treatment of arthritic rats using morphine, indomethacin and a combination of morphine and indomethacin versus controls.
Figure 3:
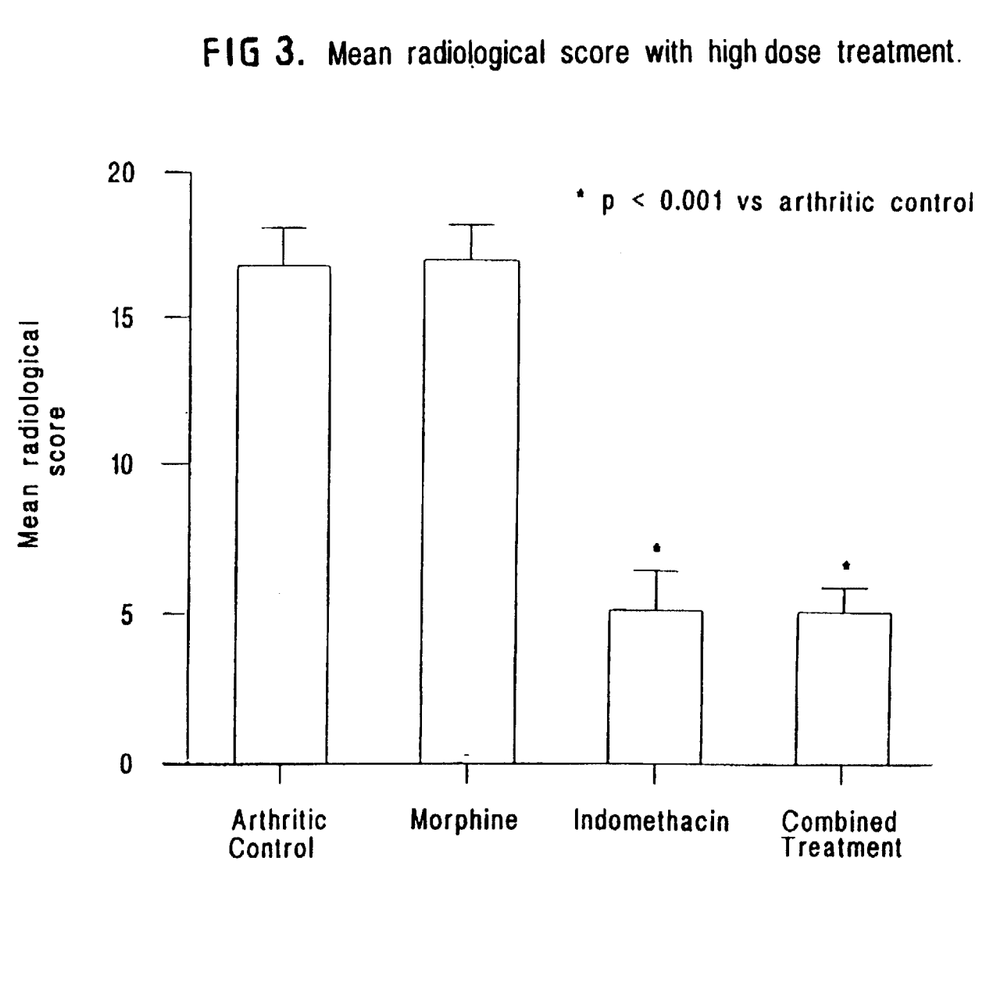
FIG. 3 is a graphical representation of mean radiological score achieved during high dose treatment of arthritic rats with morphine, indomethacin and a combination of morphine and indomethacin versus a control.
Figure 4:
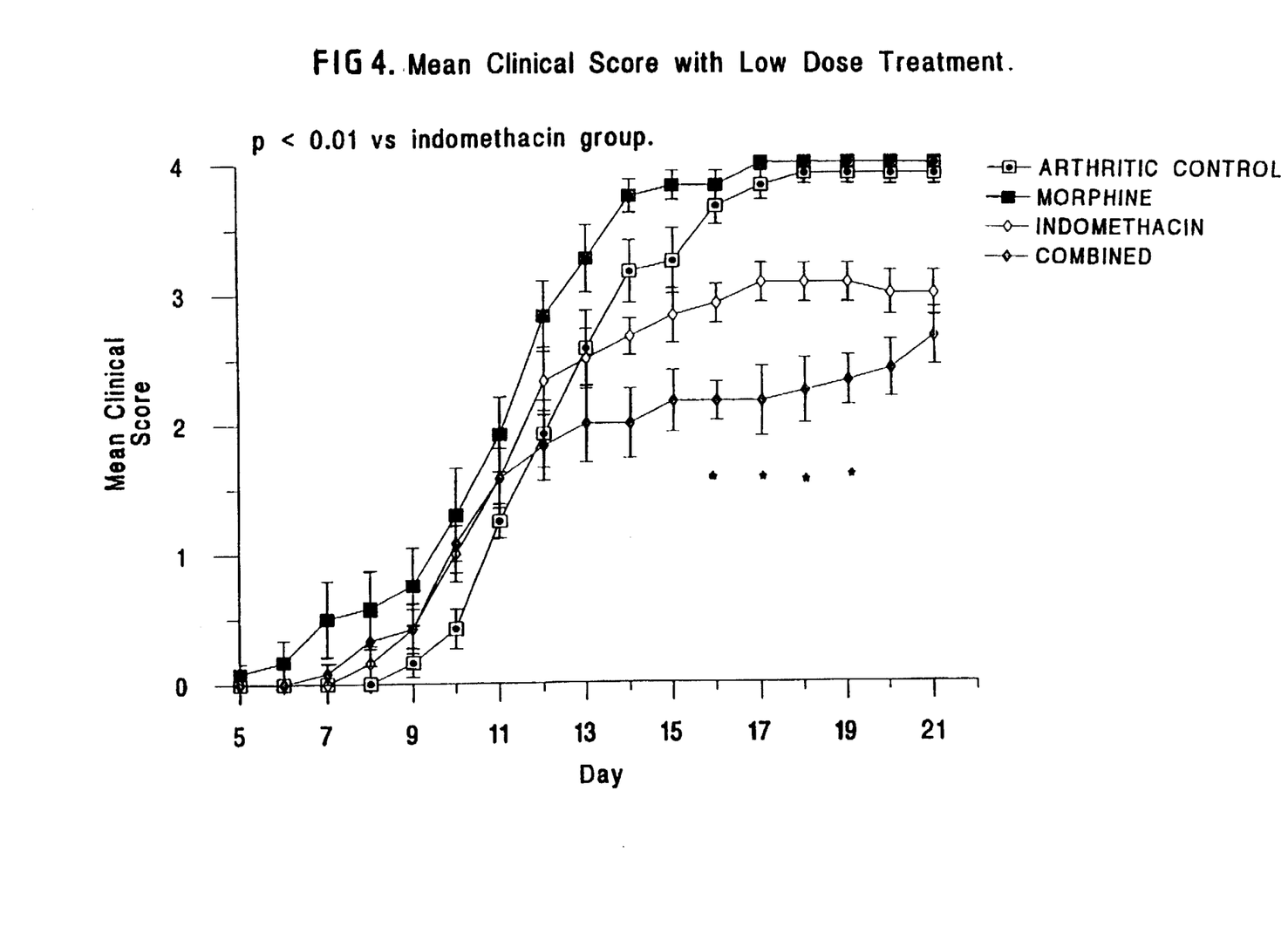
FIG. 4 is a graphical representation of the mean clinical score per day achieved during low dose treatment of arthritic rats with morphine, indomethacin and a combination of morphine and indomethacin versus a control.
Figure 5:
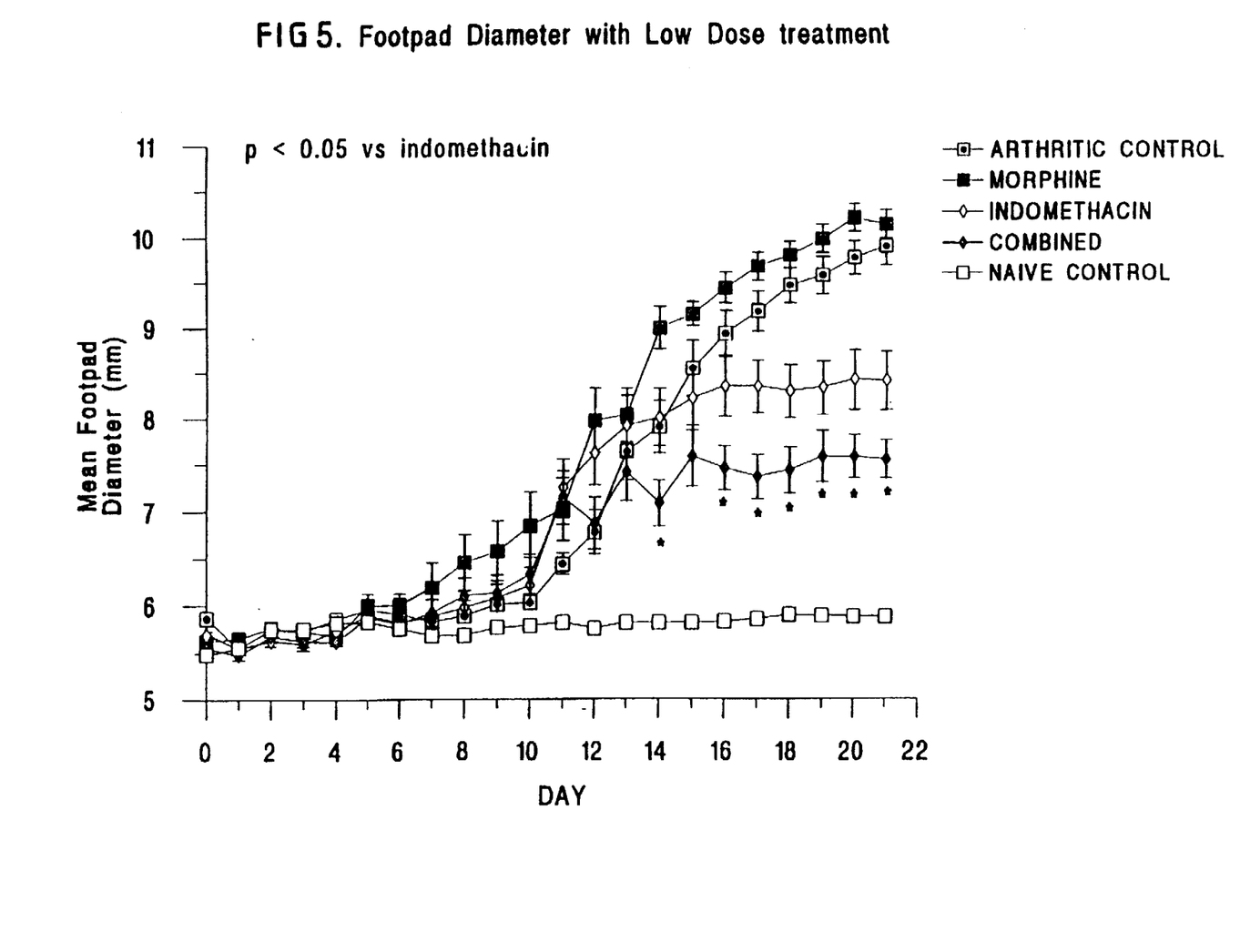
FIG. 5 is a graphical representation of the mean foot pad diameter per day achieved during low dose treatment of arthritic rats with morphine, indomethacin and a combination of morphine and indomethacin versus controls.
Figure 6:
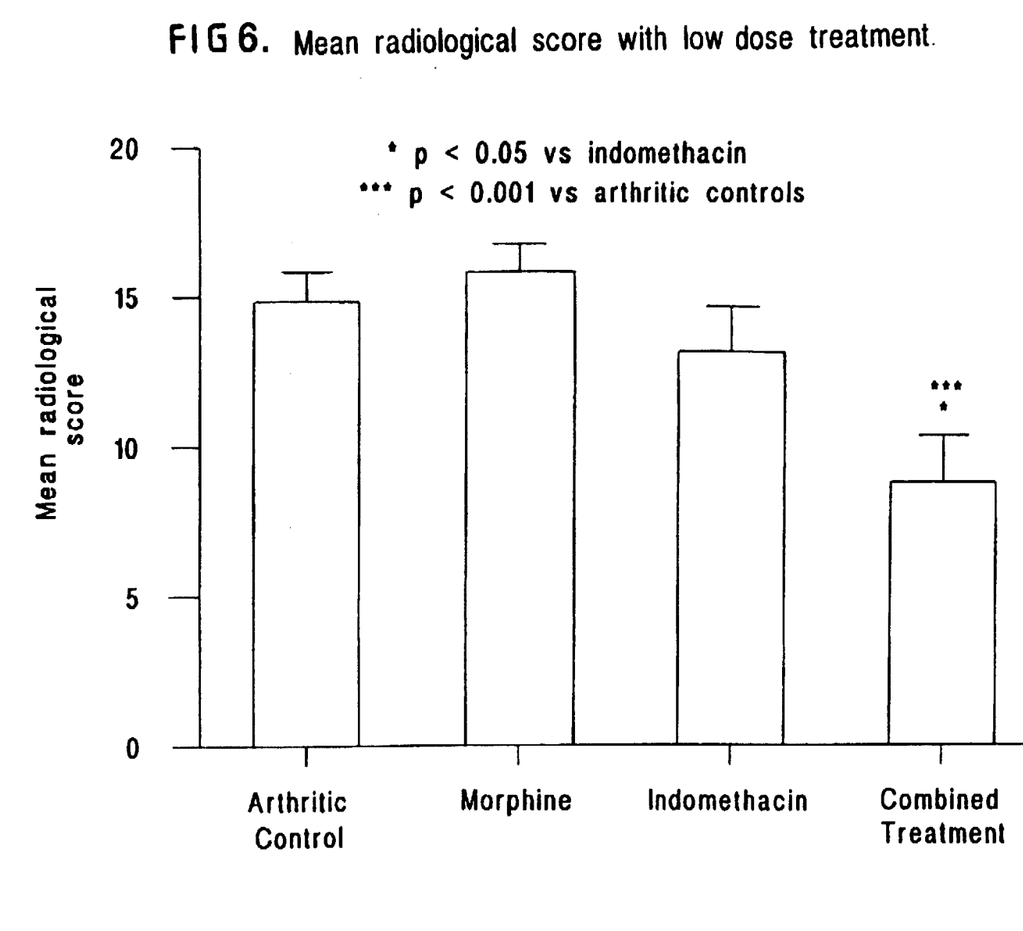
FIG. 6 is a graphical representation of the mean radiological score achieved subsequent to low dose treatment of arthritic rats with morphine, indomethacin and a combination of morphine and indomethacin versus a control.
Figure 7A:
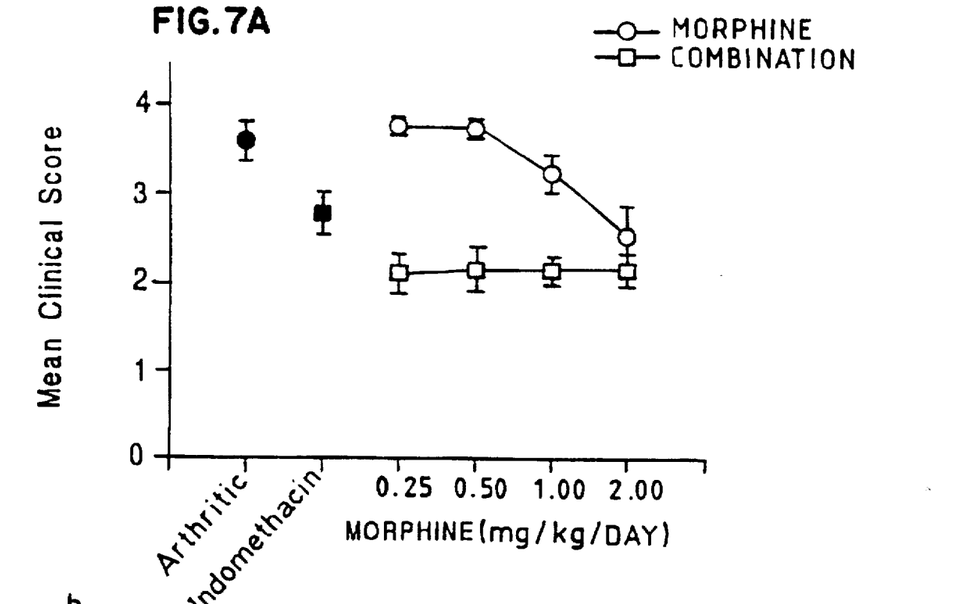
FIG. 7(a) is a graphical representation of the mean clinical score achieved during treatment of arthritic rats with indomethacin alone, morphine alone, and a combination of morphine and indomethacin versus controls.
Figure 7B:
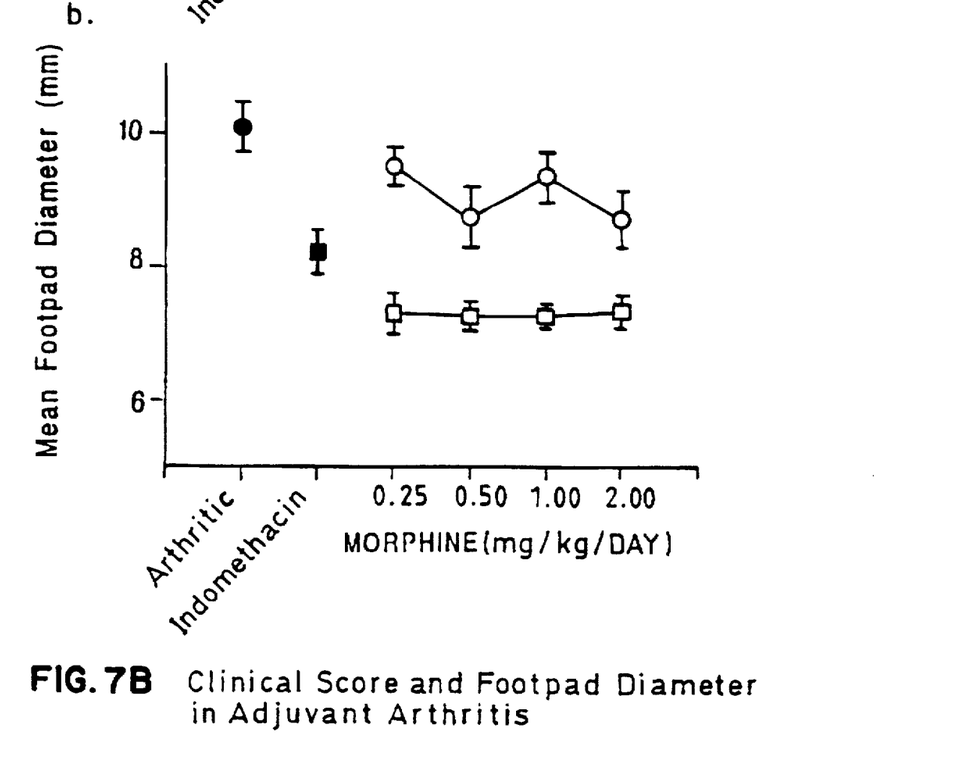
FIG. 7(b) is a graphical representation of the mean foot pad diameter achieved during treatment of arthritic rats with indomethacin alone, morphine alone, and a combination of indomethacin and morphine versus controls.
Figure 8A:
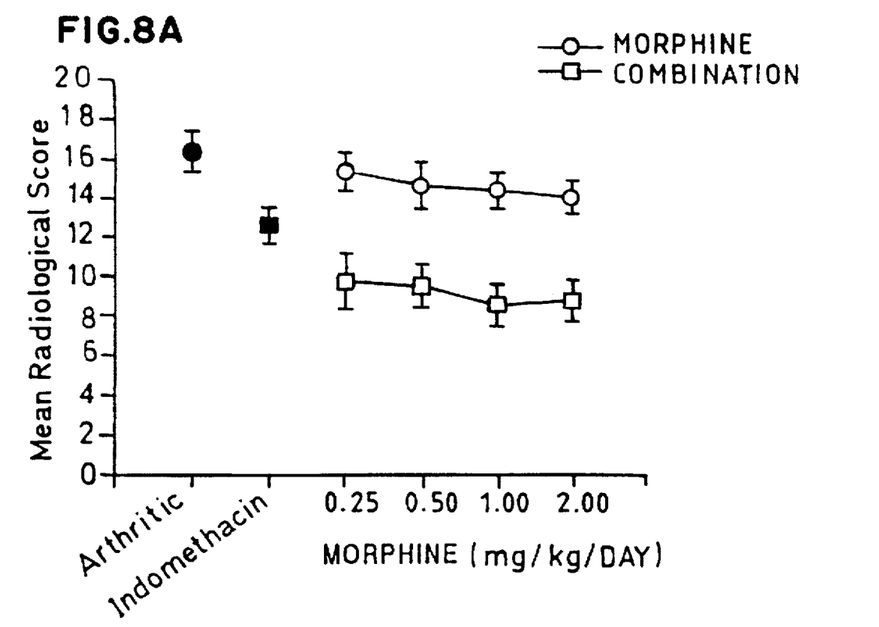
FIG. 8(a) is a graphical representation of the mean radiological score achieved from treatment of arthritic rats with indomethacin alone, morphine alone, and a combination of morphine and indomethacin versus controls.
Figure 8B:
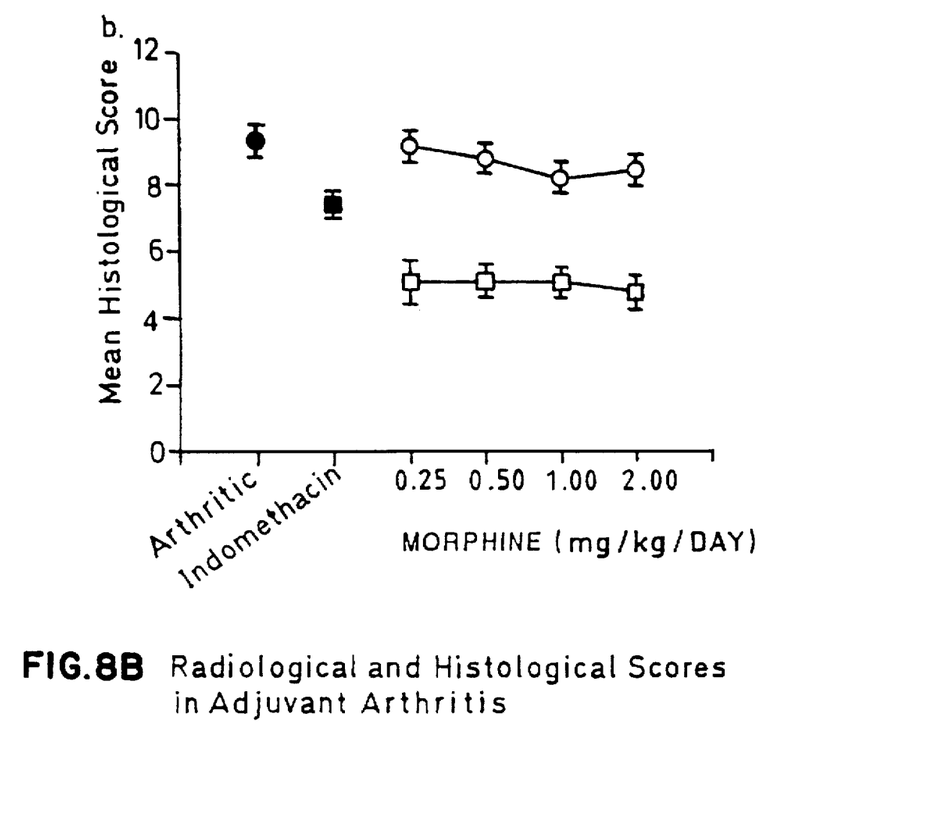
FIG. 8(b) is a graphical representation of the mean histological score achieved from the treatment of arthritic rats with indomethacin alone, with morphine alone, or a combination of indomethacin and morphine versus controls.

Combination therapy (indomethacin 0.5 mg/kg/day plus morphine 0.25; 0.50; 1.00 and 2.00 mg/kg/day) produced significant suppression of clinical score FIG. 7a, joint diameter FIG. 7b, radiological score FIG. 8a and histological score 8b when compared to untreated arthritic groups or groups treated individually with either compound. It is believed that a synergistic as opposed to an additive effect is operating.

It is observed that the suppressive effect of the combination treatment on the arthritic disease process parameters occurs over the whole range of morphine administered.

EXAMPLE 3

An MBSA study (Breckertz D. et al, Arthritis and Rheumatism, Vol 20, page 841–850, 1977) was carried out to determine the effects of opioid and non-steroidal anti-inflammatory drugs on synovial vascular responses and whether combination therapy of these compounds would have a suppressive effect on this parameter. The influence of morphine, codeine, indomethacin and ibuprofen given alone or in combination on basal extravasation was assessed.

Figure 9A:
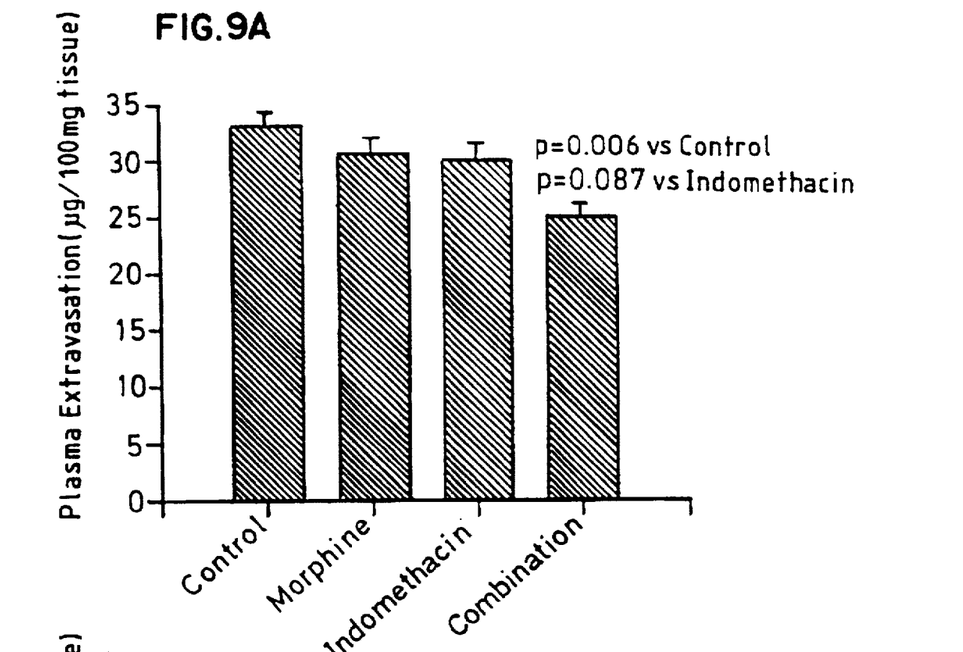
FIG. 9(a) is a graphical representation of the inhibition of plasma extravasation in 5 day mBSA arthritis treated with morphine alone, indomethacin alone, and a combination of morphine and indomethacin versus a control.

As shown in FIG. 9a morphine and indomethacin produced suppression of basal plasma extravasation which was not statistically significant whilst, in contrast, combination therapy gave significant suppression of basal plasma extravasation compared to untreated animals. The dosages made were 0.5 mg/kg/day indomethacin and 1.0 mg/kg/day morphine. As can be seen the combination therapy was more effective at reducing basal plasma extravasation compared to either drug individually.

Figure 9B:
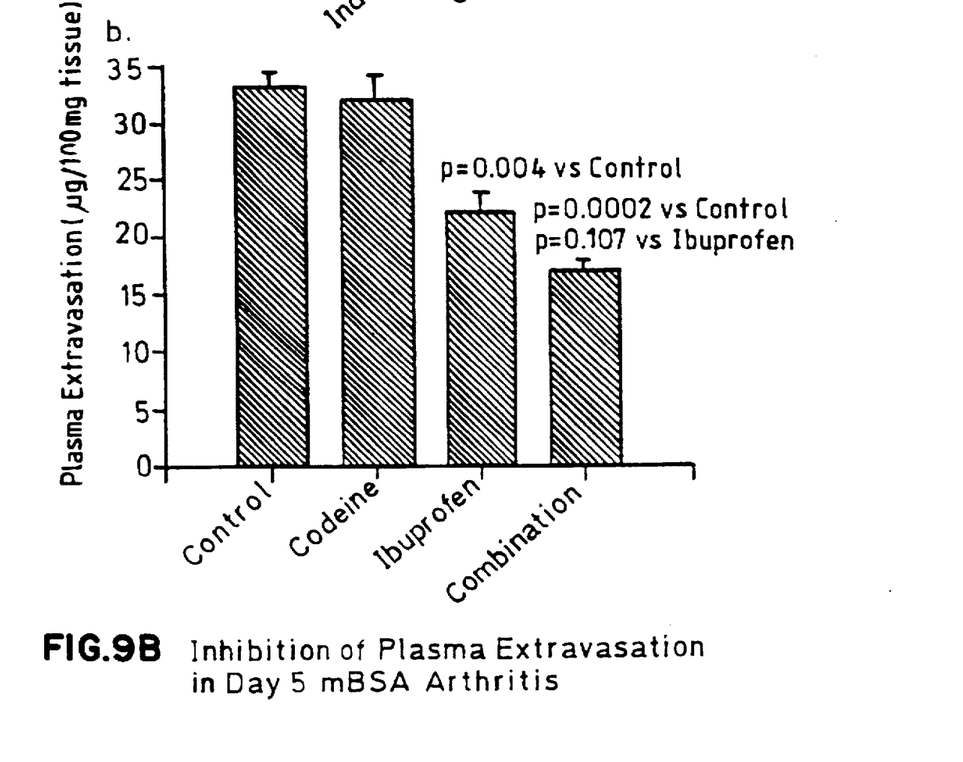
FIG. 9(b) is a graphical representation of the inhibition of plasma extravasation in 5 day mBSA arthritis treated with codeine alone, ibuprofen alone, and a combination of codeine and ibuprofen versus a control.

As shown in FIG. 9b combination therapy with oral codeine and ibuprofen also produced significant suppression of basal plasma extravasation, the results mirroring those obtained with morphine and indomethacin. The dosages used were 2.5 mg/kg/day codeine phosphate and 5 mg/kg/day ibuprofen.

The above experimental studies demonstrate that combination therapy with a non-steroidal anti-inflammatory and an opioid drug, for example, morphine and indomethacin and codeine and ibuprofen can substantially inhibit the arthritic disease process.

In particular the response between opioid and non-steroidal anti-inflammatory drugs has been found to occur in peripheral tissue and unexpectedly low doses of orally administered opioid and non-steroidal anti-inflammatory drugs can produce a surprisingly beneficial clinical effect.

In order that the invention may be well understood the following Examples of composition prepared in accordance with the invention are given by way of illustration only.

Example 1

|  | mg/Capsule |
|---|---|
| Indomethacin | 10.0 |
| Morphine sulphate | 20.0 |
| Lactose | 118.5 |
| Talc | 0.75 |
| Colloidal anhydrous silica | 0.75 |
| Total | 150.0 |

Example 2

|  | mg/Capsule |
|---|---|
| Diclofenac sodium | 75.0 |
| Codeine phosphate | 37.5 |
| Lactose | 85.5 |
| Talc | 1.0 |
| Colloidal anhydrous silica | 1.0 |
| Total | 200.0 |

Example 3

|  | mg/Capsule |
|---|---|
| Ibuprofen | 300.0 |
| Codeine phosphate | 15.0 |
| Lactose | 81.0 |
| Talc | 2.0 |
| Colloidal anhydrous silica | 2.0 |
| Total | 400.0 |

While the invention has been illustrated with respect to the production and use of a particular compound, it is apparent that variations and modifications of the invention can be made without departing from the spirit or scope of the invention.

What is claimed is:

1. A method for the inhibition of an arthritis disease process in a patient in need thereof, the method comprising:
   administering indomethacin or pharmaceutically acceptable salts thereof and morphine or pharmaceutically acceptable salts thereof, in synergistic amounts and for a duration effective to inhibit an arthritis disease process in a patient in need thereof.

2. The method according to claim 1, wherein at least one of said drugs is in a solid oral dosage form.

3. The method according to claim 1, wherein at least one of said drugs is suitable for dosing once or twice a day.

4. The method according to claim 1 wherein said indomethacin is administered in a daily dose ranging from about 5 to about 300 mg and said morphine is administered in a dose ranging from about 5 to about 300 mg.

5. The method of claim 1, wherein said arthritis disease is osteoarthritis.

6. The method of claim 1, wherein said arthritis disease is rheumatoid arthritis.

7. The method of claim 1, wherein said method results in a reduction of the mean radiological score of said patient.

8. The method of claim 3, said oral dosage form comprising 2.5 to 150 mg morphine sulfate and 2.5 to 150 mg indomethacin.

9. The method of claim 2, said oral dosage form selected from the group consisting of a syrup, suspension, linctus tablet or filled capsule.

10. The method of claim 3, said oral dosage form being formulated to provide a sustained release of at least a portion of said indomethacin or said morphine.

11. The method of claim 10, said oral dosage form further comprising a hydrophilic or hydrophopic polymer, a long chain hydrocarbon, and a polyalkylene glycol.

12. A method of reducing the mean radiological score of an arthritis patient, said method comprising
   administering synergistic effective amounts of indomethacin or pharmaceutically acceptable salts thereof and morphine or pharmaceutically acceptable salts thereof, said mean radiological score being reduced by an amount greater than the reduction of said score by the administration of morphine in the absence of indomethacin.

13. A method of reducing the mean histological score of an arthritis patient, said method comprising
   administering synergistic effective amounts of indomethacin or pharmaceutically acceptable salts thereof and morphine or pharmaceutically acceptable salts thereof, said mean histological score being reduced by an amount greater than the reduction of said score by the administration of morphine in the absence of indomethacin.

* * * * *